United States Patent [19]
Johnson

[11] Patent Number: 5,756,512
[45] Date of Patent: May 26, 1998

[54] TREATMENT OF NON-SMALL CELL LUNG CARCINOMA

[75] Inventor: Randall Keith Johnson, Ardmore, Pa.

[73] Assignee: SmithKline Beecham Corporation, Philadelphia, Pa.

[21] Appl. No.: 699,046

[22] Filed: Jul. 16, 1996

Related U.S. Application Data

[63] Continuation of Ser. No. 107,722, Aug. 20, 1993, abandoned, which is a continuation of Ser. No. 658,937, Feb. 21, 1991, abandoned.

[51] Int. Cl.$^6$ .................. A61K 31/44; A61K 31/535; A61K 31/495; A61K 31/50
[52] U.S. Cl. .................. 514/283; 514/233.2; 514/253
[58] Field of Search .................. 514/283, 233.2, 514/253

[56] References Cited

U.S. PATENT DOCUMENTS 5,004,758  4/1991  Boehm et al. .................. 514/283

*Primary Examiner*—Jerome D. Goldberg
*Attorney, Agent, or Firm*—Yuriy P. Stercho; Stephen A. Venetianer; Edward T. Lentz

[57] ABSTRACT

A method of treating non-small cell lung carcinoma in a human afflicted therewith which comprises administering to such human an effective amount of a compound of the water soluble camptothecin analog class.

13 Claims, No Drawings

TREATMENT OF NON-SMALL CELL LUNG CARCINOMA

This is a continuation of application Ser. No. 08/107,722, filed Aug. 20, 1993, now abandoned which is a continuation of PCT/US 92/01034 filed Feb. 7, 1992 which is a continuation of Ser. No. 07/658,937, filed Feb. 21, 1991, now abandoned.

BACKGROUND OF THE INVENTION

This invention relates to a method of treating non-small cell lung carcinoma in a human afflicted therewith which comprises administering to such human an effective amount of a compound of the water soluble camptothecin analog class, such as topotecan.

The structure of the DNA helix within eukaryotic cells imposes certain topological problems that the cellular apparatus must solve in order to use its genetic material as a template. The separation of the DNA strands is fundamental to cellular processes such as DNA replication and transcription. Since eukaryotic DNA is organized into chromatin by chromosomal proteins, the ends are constrained and the strands cannot unwind without the aid of enzymes that alter topology. It has long been recognized that the advancement of the transcription or replication complex along the DNA helix would be facilitated by a swivel point which would relieve the torsional strain generated during these processes.

Topoisomerases are enzymes that are capable of altering DNA topology in eukaryotic cells. They are critical for important cellular functions and cell proliferation. There are two classes of topoisomerases in eukaryotic cells, type I and type II.

Topoisomerase I is a monomeric enzyme of approximately 100,000 molecular weight. The enzyme binds to DNA and introduces a transient sinale-strand break, unwinds the double helix (or allows it to unwind), and subsequently reseals the break before dissociating from the DNA strand.

Camptothecin, a water-insoluble alkaloid produced by trees indigenous to China and India, and a few other congeners thereof, are the only class of compounds known to inhibit topoisomerase I.

Camptothecin and other topoisomerase I inhibiting congeners have not proven to be attractive for clinical drug development as cytolytic agents because of lack of clinical efficacy, unacceptable dose-limiting toxicity, unpredictable toxicity, poor aqueous solubility, and/or unacceptable shelf life stability.

Therefore, there is a need for topoisomerase I inhibiting agents which avoid the aforementioned undesirable features of camptothecin and related topoisomerase I inhibiting congeners. Topotecan, or any compound of the water soluble camptothecin analog class, is a specific inhibitor of DNA topoisomerase I which fulfills such need.

SUMMARY OF THE INVENTION

This invention relates to a method of treating non-small cell lung carcinoma in a human afflicted therewith which comprises administering to such human an effective amount of a compound of the water soluble camptothecin analog class.

This invention also relates to a method of treating non-small cell lung carcinoma in a human afflicted therewith which comprises administering to such human an effective amount of topotecan.

DETAILED DESCRIPTION OF THE INVENTION

By the term "a compound of the water soluble camptothecin analog class" is meant any compound claimed in U.S. Pat. No. 5,004,758, the entire disclosure of which is hereby incorporated by reference. The preparation of any compound of the water soluble camptothecin analog class (including pharmaceutically acceptable salts, hydrates and solvates thereof) as well as the preparation of oral and parenteral pharmaceutical compositions comprising a compound of the water soluble camptothecin analog class and an inert, pharmaceutically acceptable carrier or diluent, is extensively described in U.S. Pat. No. 5,004,758. The same extensive description is found in European Patent Application Number 88311366.4, published on Jun. 21, 1989 as Publication Number EP 0 321 122, the entire disclosure of which is hereby incorporated by reference. Preferred compounds of the water soluble camptothecin analog class include those compounds of the formula:

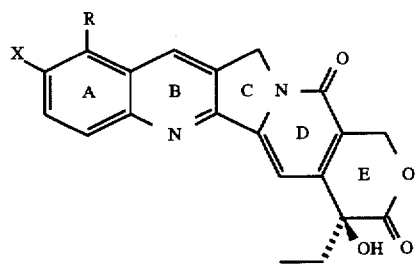

wherein:
a) X is hydroxy and R is trimethylammoniummethyl;
b) X is hydroxy and R is N-methylpiperazinylmethyl;
c) X is hydroxy and R is N-methylanilinomethyl;
d) X is hydroxy and R is cyclohexylaminomethyl;
e) X is hydroxy and R is N,N-dimethylaminoethyloxymethyl;
f X is hydroxy and R is cyclopropylaminomethyl;
g) X is hydroxy and R is morpholinomethyl;
h) X is hydroxy and R is aminomethyl; and
i) X is hydroxy and R is cyanomethyl; and
j) X is hydroxy and R is dimethylaminomethyl or any pharmaceutically acceptable salts, hydrates and solvates thereof.

Topotecan is the most preferred compound of the water soluble camptothecin analog class. By the term "topotecan" as used herein is meant the compound of the formula:

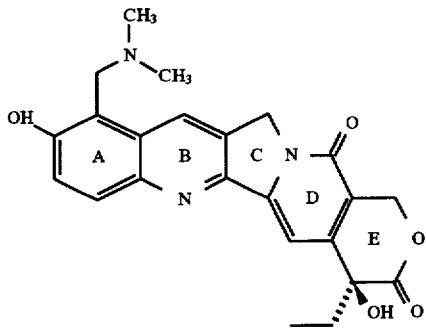

(S)-9-dimethylaminomethyl-10-hydroxycamptothecin and any pharmaceutically acceptable salt, hydrate or solvate thereof. Topotecan's chemical name is (S)-10[(dimethylamino) methyl]-4-ethyl-4,9-dihydroxyy-1H-pyrano[3',4':6,7]indolizino[1,2-b]quinolone-3,14(4H, 12H)-dione.

Topotecan is water-soluble by virtue of the presence of the basic side-chain at position 9 which forms salts with acids.

Preferred salt forms of topotecan include the hydrochloride salt, acetate salt and methanesulfonic acid salt. A alkali metal salt form of the carboxylate formed on alkaline hydrolysis of the E-ring lactone of topotecan would also yield a soluble salt, such as the sodium salt.

The preparation of topotecan (including pharmaceutically acceptable salts, hydrates and solvates thereof) as well as the preparation of oral and parenteral pharmaceutical compositions comprising topotecan and an inert, pharmaceutically acceptable carrier or diluent, is extensively described in U.S. Pat. No. 5,004,758. The same extensive description is found in European Patent Application Number 88311366.4, published on Jun. 21, 1989 as Publication Number EP 0 321 122.

This invention relates to a method of treating non-small cell lung carcinoma in a human afflicted therewith which comprises administering to such human an effective amount of a compound of the water soluble camptothecin analog class. One preferred aspect of this invention relates to a method of treating non-small cell lung carcinoma in a human afflicted therewith which comprises administering to such human an effective amount of topotecan.

By the term "non-small cell lung carcinoma" as used herein is meant any of the three subtypes thereof, i.e., adenocarcinoma of the lung, squamous cell carcinoma of the lung and large cell carcinoma of the lung.

By the term "treating non-small cell lung carcinoma" as used herein is meant the inhibition of the growth of non-small cell lung carcinoma cells. Preferably such treatment also leads to the regression of tumor growth, i.e., the decrease in size of a measurable tumor. Most preferably, such treatment leads to the complete regression of the tumor.

By the term "administering" is meant parenteral or oral administration. By "parenteral" is meant intravenous, subcutaneous and intramuscular administration.

By the term "effective amount of a compound of the water soluble camptothecin analog class" and "effective amount of topotecan" as used herein is meant a course of therapy which will result in treating non-small cell lung carcinoma. It will be appreciated that the actual preferred course of therapy will vary according to, inter alia, the mode of administration, the particular formulation of a compound of the water soluble camptothecin analog class (such as topotecan) being utilized, the mode of administration and the particular host being treated. The optimal course of therapy for a given set of conditions can be ascertained by those skilled in the art using conventional course of therapy determination tests in view of the information set out herein, as well as the information outlined in U.S. Pat. No. 5,004,758. The same information is found in European Patent Application Number 88311366.4, published on Jun. 21, 1989 as Publication Number EP 0 321 122.

For parenteral administration of a compound of the water soluble camptothecin analog class, the course of therapy generally employed is from about 0.5 to about 25.0 mg/m$^2$ of body surface area per day for about one to about five consecutive days. More preferably, the course of therapy employed is from about 1.0 to about 2.5 mg/m$^2$ of body surface area per day for about five consecutive days. Most preferably, the course of therapy employed is from about 1.5 to about 2 mg/m$^2$ of body surface area per day for about five consecutive days. Preferably, the course of therapy is repeated at least once at about a seven day to about a twenty-eight day interval (from the date of initiation of therapy) depending upon the initial dosing schedule and the patient's recovery of normal tissues. Most preferably, the course of therapy continues to be repeated based on tumor response.

Preferably, the parenteral administration will be by short (e.g., 30 minute) or prolonged (e.g., 24 hour) intravenous infusion. More preferably, the topotecan will be administered by a 30 minute intravenous infusion.

At this time, it is believed that the most preferred course of parenteral therapy to be employed with topotecan for a previously non-treated or lightly pretreated patient is an initial course of therapy of 1.5 mg of topotecan/m$^2$ of body surface area per day administered by short intravenous infusion for five consecutive days. When the patient has recovered sufficiently from the drug-related effects of this initial course, an additional course of therapy of 2.0 mg of topotecan/m$^2$ of body surface area per day is administered by short intravenous infusion for five consecutive days, to be repeated based on tumor response.

At this time, it is believed that the most preferred course of parenteral therapy to be employed with topotecan for a heavily pretreated patient is an initial course of therapy of 1.0 mg of topotecan/m$^2$ of body surface area per day administered by short intravenous infusion for five consecutive days. When the patient has recovered sufficiently from the drug-related effects of this initial course, an additional course of therapy of 1.5 mg of topotecan/m$^2$ of body surface area per day is administered by short intravenous infusion for five consecutive days, such course of therapy to be repeated based on tumor response.

For oral administration of a compound of the water soluble camptothecin analog class, the course of therapy generally employed is from about 1.0 to about 50.0 mg/m$^2$ of body surface area per day for about one to five consecutive days. More preferably, the course of therapy employed is from about 1.5 to about 5.0 mg/m$^2$ of body surface area per day for about five consecutive days. Preferably, the course of therapy is repeated at least once at about a seven day to about a twenty-eight day interval (from the date of initiation of therapy) depending upon the initial dosing schedule and the patient's recovery of normal tissues. Most preferably, the course of therapy continues to be repeated based on tumor response.

CLINICAL PHARMACEUTICAL INFORMATION

Topotecan is currently undergoing Phase I clinical investigation. The following pharmaceutical information is being supplied to the clinicians:

How supplied—As a vial containing 5 mg (of the base) with 100 mg mannitol. The pH is adjusted to 3.0 with HCl/NaOH. Lyophilized powder is light yellow in color. Intact vials should be stored under refrigeration (2–8 degrees Centigrade).

Solution Preparation—When the 5 mg vial is reconstituted with 2 ml of Sterile Water for Injection, USP, each ml will contain 2.5 mg of topotecan as the base and 50 mg of mannitol, USP. Topotecan must not be diluted or mixed with buffered solutions because of solubility and stability considerations.

Stability—Shelf life surveillance of the intact vials is ongoing. Because the single-use lyophilized dosage form contains no antibacterial preservatives, it is advised that the reconstituted solution be discarded eight hours after initial entry into the vial. Further dilutions of the reconstituted solution to concentrations of 0.02 mg/ml and 0.1 mg.ml in 5% Dextrose Injection, USP, ("D5W") or 0.9% Sodium Chloride Injection, USP, ("NS") in plastic bags stored at room temperature yielded the following stability results:

PERCENTAGE OF INITIAL TOPOTECAN
REMAINING IN SOLUTION

|        |            | Concentration |           |
| ------ | ---------- | ------------- | --------- |
| Diluent | Time (hrs) | 0.02 mg/ml   | 0.1 mg/ml |
| D5W    | 0          | 100.00        | 100.00    |
|        | 6          | 99.29         | 99.68     |
|        | 24         | 102.30        | 98.16     |
|        | 48         | 101.98        | 97.91     |
| NS     | 0          | 100.00        | 100.00    |
|        | 6          | 98.58         | 97.71     |
|        | 24         | 96.01         | 98.30     |
|        | 48         | 102.03        | 98.35     |

Topotecan diluted in saline (10 ug/ml or 500 ug/ml) or dextrose (6.7 ug/ml or 330 ug/ml) is stable in a hang-bag for 24 hours with at least 95% recovery.

Treatment dose—The treatment dose is to be diluted in a final volume of 150 ml of Sodium Chloride Injection, USP (without preservatives) and administered over a 30 minute period. The treatment dose is to be kept under refrigeration and protected from light and it is to be used within 24 hours.

Utility

One human patient with metastatic non-small cell lung carcinoma, who was refractory to pretreatment with VP-16 (etoposide) and cisplatin, received a course of therapy comprising intravenous administration of 1.5 mg of topotecan/m$^2$ of body surface area per day for five consecutive days. This course of therapy was repeated at least five more times at twenty-one day intervals (from the date of initiation of therapy) for a total of at least six to four treatments. Tumor size regression was evaluated by CAT (computerized axial tomography) scan. After the above-outlined six treatment regimen, a complete regression of the disease was observed, i.e., all tumors had disappeared and no evidence of clinical disease was present.

In addition, a temporary response (measurable tumor size regression) was observed in a patient with non-small cell lung carcinoma who had received at least one course of therapy comprising intravenous administration of 1.5 mg of topotecan/m$^2$ of body surface area per day for five consecutive days. Such patient had previously received radiation and failed to respond to the investigational agent ipomeanol.

What is claimed is:

1. A method of treating non-small cell lung carcinoma in a human afflicted therewith which comprises administering to such human an effective amount of a compound of the formula:

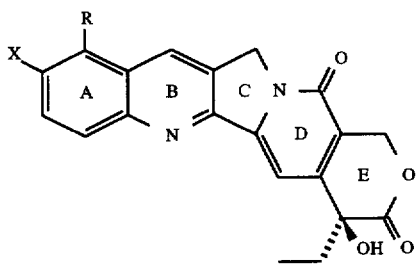

wherein:
a) X is hydroxy and R is trimethylammoniummethyl;
b) X is hydroxy and R is N-methylpiperazinylmethyl;
c) X is hydroxy and R is N-methylanilinomethyl;
d) X is hydroxy and R is cyclohexylaminomethyl;
e) X is hydroxy and R is N,N-dimethylaminoethyloxymethyl;
f) X is hydroxy and R is cyclopropylaminomethyl;
g) X is hydroxy and R is morpholinomethyl;
h) X is hydroxy and R is aminomethyl;
i) X is hydroxy and R is cyanomethyl; or
j) X is hydroxy and R is dimethylaminomethyl or any pharmaceutically acceptable salts, hydrates and solvates thereof; wherein the course of therapy employed is from about 1.0 to about 2.5 mg/m$^2$ of body surface area per day for about five consecutive days.

2. The method of claim 1 wherein the administration is oral.

3. The method of claim 1 wherein the administration is parenteral.

4. The method of claim 3 wherein the course of therapy employed is from about 1.5 to about 2 mg/m$^2$ of body surface area per day for about five consecutive days.

5. The method of claim 4 wherein the course of therapy is repeated at least once at about a seven day to about a twenty-eight day interval.

6. The method of claim 3 wherein the administration is via short or long intravenous infusion.

7. The method of claim 6 wherein the administration is via a 30 minute intravenous infusion.

8. The method of claim 6 wherein the administration is via a 24 hour intravenous infusion.

9. The method of claim 6 wherein the compound is topotecan.

10. The method of claim 1 wherein the compound is topotecan.

11. The method of claim 1 wherein the non-small cell lung carcinoma is adenocarcinoma of the lung.

12. The method of claim 1 wherein the non-small cell lung carcinoma is squamous cell carcinoma of the lung.

13. The method of claim 1 wherein the non-small cell lung carcinoma is large cell carcinoma of the lung.

* * * * *